United States Patent
Haselman et al.

(10) Patent No.: US 11,980,385 B2
(45) Date of Patent: May 14, 2024

(54) DRIVE SHAFT DESIGN, CONDITIONING AND STABILIZATION METHODS FOR ROTATIONAL MEDICAL DEVICES

(71) Applicant: Cardiovascular Systems, Inc., St. Paul, MN (US)

(72) Inventors: Benjamin D. Haselman, St. Paul, MN (US); Tristan A. Van de Moortele, Minneapolis, MN (US); Matthew W. Hanson, St. Louis Park, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 191 days.

(21) Appl. No.: 17/650,565

(22) Filed: Feb. 10, 2022

(65) Prior Publication Data
US 2022/0249122 A1    Aug. 11, 2022

Related U.S. Application Data

(60) Provisional application No. 63/148,425, filed on Feb. 11, 2021.

(51) Int. Cl.
*A61B 17/3207*    (2006.01)
*A61M 60/804*    (2021.01)
*A61M 60/818*    (2021.01)

(52) U.S. Cl.
CPC ... *A61B 17/320758* (2013.01); *A61M 60/804* (2021.01); *A61M 60/818* (2021.01); *A61B 2017/320775* (2013.01)

(58) Field of Classification Search
CPC ........... A61B 17/320758; A61B 2017/320775; A61B 2017/320032; A61M 60/804; A61M 60/818
See application file for complete search history.

(56) References Cited

U.S. PATENT DOCUMENTS 5,695,506 A    12/1997    Pike et al.
7,507,245 B2    3/2009    Shturman et al.
(Continued)

FOREIGN PATENT DOCUMENTS

WO    WO-2004080345 A2 *    9/2004    ....... A61B 17/32002

OTHER PUBLICATIONS

International Search Report and Written Opinion issued in PCT Application No. PCT/US2022/70621 and dated Apr. 13, 2022.

*Primary Examiner* — Tuan V Nguyen
(74) *Attorney, Agent, or Firm* — Kagan Binder, PLLC

(57) ABSTRACT

A flexible drive shaft assembly is provided for an intravascular medical device, for example and without limitation, a blood pump, a rotational atherectomy device, or a rotational thrombectomy device. The blood pump embodiment provides an electric motor and a rotational impeller, with a rotational drive shaft disposed therebetween and configured to rotationally drive the impeller. The drive shaft is moved from an undeformed length to a deformed length when connected between the electric motor and the rotational impeller to provide a biasing force on the rotational impeller in the proximal direction to maintain the impeller in a desired axial or linear location. In other embodiments, drive shaft comprises a proximal section with a length and a spring constant and a distal section of relatively longer length and a relatively higher spring constant. In other embodiments, hypotube(s) and/or support mandrel(s) may be provided.

20 Claims, 2 Drawing Sheets

(56) References Cited

U.S. PATENT DOCUMENTS

| | | |
|---|---|---|
| 8,388,565 B2 | 3/2013 | Shifflette |
| 10,668,195 B2 | 6/2020 | Flores |
| 2015/0005791 A1 | 1/2015 | Schoenle et al. |
| 2018/0258979 A1 | 9/2018 | Omohundro et al. |

* cited by examiner

DRIVE SHAFT DESIGN, CONDITIONING AND STABILIZATION METHODS FOR ROTATIONAL MEDICAL DEVICES

CROSS-REFERENCE TO RELATED APPLICATIONS

This application claims priority to provisional application Ser. No. 63/148,425, filed Feb. 11, 2021 and entitled DRIVE SHAFT DESIGN, CONDITIONING, SECUREMENT METHODS FOR HEMODYNAMIC SUPPORT DEVICE, the entire contents of which are incorporated herein by reference.

STATEMENT REGARDING FEDERALLY SPONSORED RESEARCH OR DEVELOPMENT

Not Applicable

BACKGROUND OF THE INVENTION

Field of the Invention

Rotational medical devices configured for intravascular use and having an external motor configured to rotatingly drive a drive shaft having a tool at or near a distal end of the drive shaft.

Description of the Related Art

Generally, rotational medical devices for intravascular use comprise an externally located motor with a driven rotational drive shaft attached thereto and a tool at or near a distal end of the drive shaft, e.g., an atherectomy device as, e.g., in U.S. Pat. No. 6,494,890 incorporated herein by reference in its entirety. In addition, in hemodynamic devices such as blood pumps, e.g., ventricular assist pump devices transmit torque generated by an electric motor located external to the patient's body. In this case, the connected electric motor generates torque along a rotational drive shaft which is, in turn, rotationally and operationally connected with the blood pump impeller located within the patient's body. In other cases, the electric motor may also be located within the patient's body, i.e., implantable, and configured to rotate an impeller of an implanted blood pump.

In at least the case of the electric motor located outside of the patient's body, the axial position of the pumping impeller should be controlled. Generally, in such devices, the impeller is prevented or restrained from moving proximally by a combination of the outer sheath surrounding the impeller and the bearing supporting the rotating impeller and the bearing housing surrounding the rotating impeller and supporting bearing. However, the impeller in this device is prevented generally from moving in a proximal, distal, i.e., axial, direction only by the drive shaft that is connected at its proximal end to the electric motor and connected at its distal end with the rotating impeller. Known drive shafts experience forces that cause a change in the positioning of the distal end of the drive shaft, for example and without limitation, winding and/or unwinding of the drive shaft during rotation. The events and resulting forces causing movement in location of the distal end of the drive shaft may occur during, e.g., and without limitation, startup and/or as a result of rotational speed changes necessitated by resultant blood flow generated by the blood pump. Winding and/or unwinding of the drive shaft in these cases will cause a shortening and/or lengthening of the known drive shaft and, in turn, a corresponding axial movement of the distal end of the drive shaft and the impeller connected thereto. In some cases, the distal end of the drive shaft, and the impeller connected thereto, may move in a radial direction relative to a nominal axis of the drive shaft. Any of these impeller movement events are highly undesirable as measured parameters such as flow volume and rate may be affected. In extreme cases, measured parameters may exceed established thresholds and an alarm may be triggered in response.

The issues that are described herein may present generally in rotational medical devices with elongated flexible drive shafts for intravascular use and having tools disposed on or near a distal end of the drive shaft. For example, and without limitation, rotational atherectomy devices, thrombectomy devices and blood pumps may benefit from the various embodiments described below.

The various inventions disclosed herein address these, inter alia, issues.

BRIEF DESCRIPTION OF THE SEVERAL VIEWS OF THE DRAWINGS

These drawings are exemplary illustrations of certain embodiments and, as such, are not intended to limit the disclosure.

DETAILED DESCRIPTION OF THE INVENTION

With reference to the Figures, inventions are disclosed that ensure that an elongated flexible drive shaft attached to an external motor, e.g., an electrical motor or turbine or the like, having a tool at or near the distal end of the drive shaft maintains a fixed position at the distal end, i.e., the axial location of the tool is fixed. For example, rotational atherectomy devices, thrombectomy devices and blood pumps, e.g., a ventricular assist device ("VAD") may benefit from some or all of the embodiments disclosed herein.

Generally, the disclosure describes solutions with reference to blood pumps, but the skilled artisan will certainly understand that some or all may be applied to other device such as rotational atherectomy and thrombectomy devices.

Thus, the various embodiments taught herein relating to blood pumps work to maintain impeller positioning, particularly in the proximal and distal, i.e., axial direction, during rotation of the drive shaft that is connected with an electric motor positioned outside of the patient's body. In this case, the blood pump and connected drive shaft traverse the patient's vasculature to the location of interest, wherein a proximal end of the drive shaft extends outside of the patient's body and is rotationally connected with the electric motor.

Figure 1:
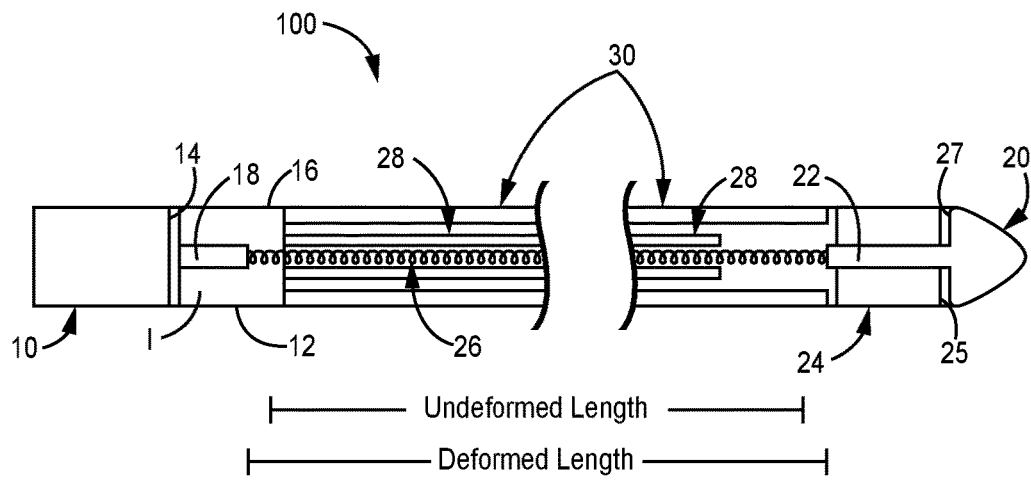
FIG. 1 illustrates a side cutaway view of one embodiment of the present invention.

As shown in FIG. 1, an exemplary blood pump system 100 comprises an electric motor 10 (located external to the patient), a motor manifold 12 defining a proximal end 14, a distal end 16, and an at least partially hollow interior region I therein. As shown, a motor rotor or shaft 18 is rotationally connected with the electric motor 10 and extends away from the motor 10 and through the proximal end 14 of the motor manifold 12 into interior region I. Proximal end 14 of manifold 12 is shown spaced apart from the motor 10, however in other embodiments such spacing may not be required.

Blood pump system 100 further comprises an impeller 20 having an impeller shaft 22 extending proximally from the impeller 20 toward the manifold 12 and motor shaft 18. An impeller housing 24 is provided and configured to surround at least a part of the impeller shaft 22, wherein in some embodiments and as illustrated, a proximal portion of the impeller shaft 22 is not covered or surrounded by the impeller housing 24. In some embodiments, the impeller shaft 22 may be completely surrounded by the impeller housing 24 such that the impeller shaft 22 is accessible for rotational connection with an elongated flexible drive shaft or cable 26.

System 100 thus comprises an elongated flexible drive shaft 26 that is rotationally connected at a proximal end with motor shaft 18 and at a distal end connected with the impeller shaft 22, wherein rotational movement and torque is transferred from the motor shaft 18 through the drive shaft 26 to the impeller shaft 22 thus causing the impeller 20 to rotate at the substantially the same speed as the motor shaft 18 and drive shaft 26.

Drive shaft 26 may be coupled or connected with the motor shaft 18 and the impeller shaft 22 by a coupler or may be welded or otherwise fixedly connected with the motor shaft 18 and impeller shaft 22 as is well known in the art.

An inner sheath 28 connected to a portion of the distal end 16 of manifold 12 and surrounds the drive shaft moving in the distal direction. As illustrated, the inner sheath 28 does not extend or surround the entire length of the drive shaft 26, instead terminating at a point that is proximal to the connection between the distal end of the drive shaft 26 and the impeller shaft 22. In other embodiments, inner sheath 28 may extend to cover the entire length of the drive shaft 26.

An outer sheath 30 is connected to a portion of the distal end 16 of manifold 12 and connected to a proximal end of the impeller housing 24, effectively surrounding the inner sheath 28 and the drive shaft 26.

To maintain the distal axial position of the distal end of the drive shaft 26 and, in turn, the impeller 20 that is connected, via the impeller shaft 22, with the distal end of the drive shaft 26, i.e., prevent axial translation thereof, the drive shaft 26 is subjected to an deforming axial, or stretching, lengthening or tension, referred to herein as "build tension". This tensioning provides a slightly, or more than slightly, deformed, lengthened and stretched drive shaft 26 between the connection of the drive shaft 26 with the motor shaft 18 and the impeller shaft 22. In turn, the deformed, stretched drive shaft provides a biasing force pulling the impeller 20 in the proximal axial direction, thereby pulling the proximal surface 27 of impeller 26 in the proximal direction to the fixed and desired location against the inner surface or inner face 25 of the impeller housing 24. In some embodiments, a bearing may interpose between inner surface 25 of impeller housing 24 and proximal surface 27 of impeller. In these embodiments, the impeller's proximal surface will be held against the inner surface 24 of impeller housing by the biased build tensioning force generated by the deformed, stretched drive shaft 26. For example, and without limitation, a ring bearing (not shown) may be bonded or attached to proximal surface 27 of impeller 20. In other embodiments, a bearing sleeve (not shown) may also be provided wherein the impeller shaft 22 rotates inside the bearing sleeve.

The motor shaft 18 to which the proximal end of the drive shaft 26 is connected may be fixed in positional location and the impeller housing 24 provides a structure with fixed location in some embodiments as the impeller is connected with the outer sheath 30 which is, in turn, connected with the manifold 12, so that the impeller 20 cannot move further in the proximal direction once the proximal surface of the impeller 20 is biased into contact against the impeller housing's proximal inner surface 25. This arrangement therefore helps to ensure that the drive shaft 26 maintains the desired position of the impeller 20 in at least the axial direction by minimizing and/or preventing impeller 20 movement or translation at least in the distal direction. The deformed, stretched drive shaft 26 may comprise a deformed, biasing-force structure that may be elastically, or may be non-elastically, deformed.

In some embodiments, the proximal end of the outer sheath 30 may be initially slidable proximally or distally within or through the hollow interior I defined within the manifold, and which may in some embodiments comprise a separate hollow channel configured to receive the outer sheath 30, so that the outer sheath 30 may be pulled or slid within the manifold 12 in the proximal or distal direction, wherein the drive shaft 26 is connected to the non-translating motor shaft 18. Pulling or sliding or translating the outer sheath 30 in the proximal direction toward motor 10 will shorten or compress the drive shaft 26, while translating the outer sheath in the distal direction will length and extend the drive shaft 26. The extension or lengthening of drive shaft 26 may achieve a desired deformed stretched configuration made possible by application of a predetermined tensioning, lengthening or stretching force which may be measured in real time by known techniques, e.g., a strain gauge or the like. Once the predetermined tensioning force is reached, the outer sheath 30 may then be fixedly, e.g., glued, to the manifold 12 to fix the axial positions of the manifold 12, the outer sheath 30, and the impeller housing 24 while providing the desired biasing build tension force on the impeller 20 in the proximal direction.

The deforming predetermined build tension force may be within the range of 20 grams of tension to 500 grams of tension. A preferred predetermined build tension force may be within the range of 220 grams to 240 grams, with a target of 230 grams. Notwithstanding the foregoing, the skilled artisan will recognize that other build tensions may be used to achieve the inventive objectives.

In some embodiments, the deformed, stretched drive shaft 26 may work to compress the outer sheath 30 which, in turn, results in a decrease of the deforming build tension force. For example, a predetermined build tension force of 230 grams may, after compression of the outer sheath 30, actually provide a drive shaft 26 deforming build tension of approximately 180 grams. In other embodiments, the outer sheath 30 may be constructed to not be compressed by the predetermined amount of build tension force wherein the predetermined build tension force target is not, or is only slightly, reduced.

Thus, in general, the predetermined build tension force target may be reduced due to outer sheath 30 compression in some embodiments. This is because compression of the outer sheath 30 ultimately reduces the length of the deformed, stretched drive shaft 26, thereby reducing the biasing stretched force on the drive shaft 26 between the impeller 20 and the manifold 12.

In other embodiments, the distance between the manifold 12 and the impeller housing 24 may be fixed and known as are the relative locations of the motor shaft 18 and the impeller shaft 22 to which the proximal and distal ends, respectively, of the drive shaft 26 are connected. The length of the drive shaft 26 may be selected to be shorter than the distance between the fixed connection locations at the motor shaft 18 and the impeller shaft 22 in order to provide a predetermined amount of biasing build tension force due to the stretched deformation of the drive shaft 26 fixed between the motor shaft 18 and the impeller shaft 22.

At least the inner sheath 28, outer sheath 30 and drive shaft 26 may be curved to accommodate the patient's vasculature during translation therethrough. Because of this curvature, gaps between the drive shaft 26 and the inner sheath 28 may cause the build tension in the drive shaft 26 to decrease. The build tension must therefore be sufficiently high so that the impeller 20 remains in its fixed, desired axial position. i.e., no distal axial translation through the full range of bending and rotational use.

Moreover, known drive shafts 26 may tend to naturally elongate slightly when put under rotational tension, particularly at relatively high rotational speeds and when subjected to a distal load such as an impeller 20, atherectomy abrading head or thrombectomy device, rotating in a fluid, e.g., a blood, environment. This phenomenon is known as "constructional stretch". This constructional stretch or elongation of drive shaft 26 may not be recoverable or reversible and results in the impeller 20 being more free to move axially during rotation. i.e., the impeller 20 may be held less tightly in the desired axial location by the now-elongated drive shaft 26 as a result. To mitigate this issue, the drive shaft 26 may be subjected to a cyclic stretching process comprising at least one stretch and relax cycle prior to being built into the final blood pump device 100. For example, the drive shaft 26 may be stretched or elongated by an axially applied force that is greater than. e.g., approximately twice (2×) or in some cases more or less than 2×, the predetermined build tension force target discussed above, and then the stretching tension is slowly released. When completely relaxed, one cycle is complete. This process may be repeated more than once. e.g., 2-4 times to minimize and/or remove the constructional stretch potential in the drive shaft 26.

In certain embodiments, the drive shaft 26 may simply be cyclically stretched as described by applying an axially applied force that is sufficient to stretch the drive shaft 26 axially to a length that is greater than the installed length of the drive shaft 26. i.e., the length of the drive shaft 26 between the attachments at the motor shaft 18 and the impeller shaft 22 when those attachments are fixed in axial position.

The cyclical stretching to minimize or eliminate constructional stretching may be done either alone, or in combination with the above-described build tensioning deforming process.

The skilled artisan will appreciate that the above-described cyclical stretching process and related benefits will readily apply to rotational atherectomy and thrombectomy drive shafts. An exemplary thrombectomy system with rotational drive shaft is disclosed in U.S. application Ser. No. 17/407,468, filed Aug. 20, 2021, and entitled "Systems, Methods and Devices for Removal of Thrombus and/or Soft Plaque with Asymmetric Mass Distribution with Working Region of Impeller", the entire contents of which is incorporated herein by reference. Further, an exemplary rotational atherectomy device is disclosed in U.S. Pat. No. 10,517,631, issued Oct. 31, 2019, the entire contents of which is incorporated herein by reference.

Figure 2:
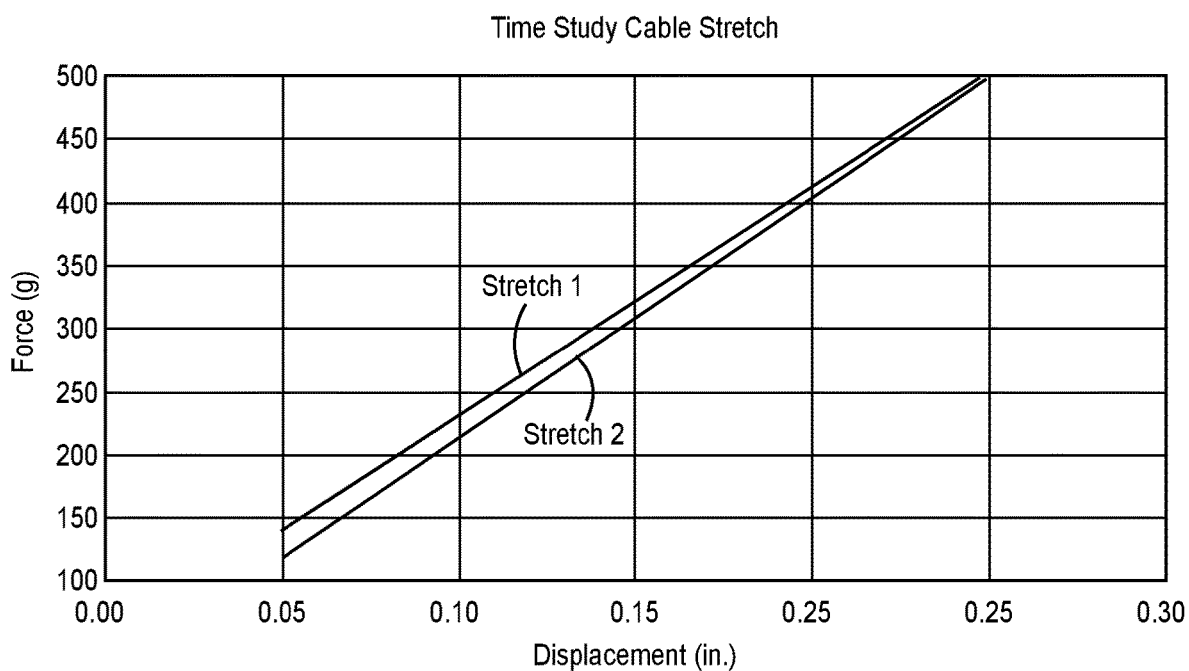
FIG. 2 illustrates a force vs displacement graph illustrating one embodiment of the present invention.

FIG. 2 illustrates a time study drive shaft subjected to the cyclic stretching process for minimizing and/or removing constructional stretch in the drive shaft using the build tensioning target to determine the stretched target force. Thus, the subject drive shaft is stretched to a target force, e.g., 2× the build tension, one or more times before accepting the drive shaft for further assembly. The target force may be greater than, equal to, or less than twice (2×) the build tension and, as discussed above, the cyclic stretching may be done once or more than once to achieve the required result. For example, the cyclic stretching may comprise stretching the shaft axially to 200-600 g and back to 0 g, from one to eight cycles, prior to assembly. FIG. 2 illustrates an exemplary cyclic stretch 1 and stretch 2 wherein an axially applied force is applied to the shaft so that the shaft is under 175 g+/−20 g stretching tension when the rotational axis of the assembly is held in a straight line. In addition, the drive shaft may be stretched without regard to a build tensioning target and simply stretched to a length greater than an installed length of the drive shaft as described above.

Figure 3:
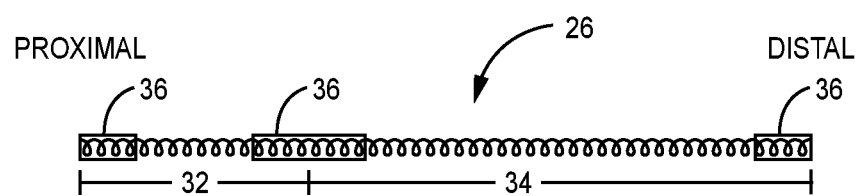
FIG. 3 illustrates a side partial cutaway view of one embodiment of the present invention.
Figure 4:
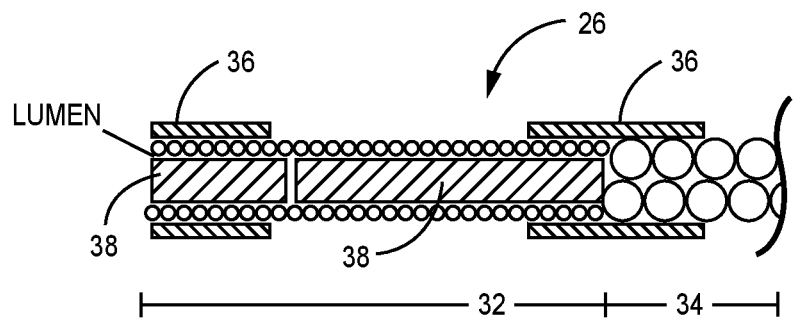
FIG. 4 illustrates a side partial cutaway view of one embodiment of the present invention.

FIGS. 3 and 4 illustrate a drive shaft 26 with a proximal section 32 having a lower spring constant relative to a distal section's 34 higher spring constant, wherein the higher spring constant of the distal section makes the distal section harder to stretch, or shorten, relative to the lower spring constant proximal section. It is understood that drive shaft 26 may be used in the same manner as described in connection with FIG. 1, thus the connections and system 100 components described therein also apply to FIGS. 3 and 4. Generally, the length of proximal section 32 may be relatively short, extending distally away from the motor rotor 18 and, in some cases a short distance distally away from the motor manifold 12.

The distal section 34 with relatively higher spring constant thus extends from the proximal section 32 to connect with the impeller shaft 22 as described above. The higher spring constant of the distal section 34 of the drive shaft 26 is desirable as it provides better fatigue and runs a much longer length than the proximal section 32 of the drive shaft 26 and, as discussed, distal section 34 is more resistant to elongation or shortening than the proximal section 32. The spring constant differential described herein may be achieved in a number of ways, including but not limited to, providing materials that have inherently different spring constants, providing a denser winding of wire filars at the distal section as compared with the proximal section; providing oppositely wound filars at the distal end; connecting one or more adjacent wire coils within the distal end to prevent them from stretching apart.

As shown in FIGS. 3 and 4, at least one hypotube 36 comprising a length that is shorter than the length of the proximal section 32 and/or the length of the distal section 34 may be attached. e.g., swaged or other known method of attachment, over the drive shaft 26 in order to eliminate or mitigate the undesirable constructional stretch described above. As in FIG. 3, the hypotubes are attached over a plurality of wire turns or filars of the drive shaft 26 of the proximal section 32 of relatively lower spring constant and/or the distal section 34. When applied to the proximal section 32, the length of the proximal section 32 that may be elongated during rotation is shortened as the region(s), e.g., the wire filars of the drive shaft 26, of the proximal section 32 covered by the hypotubes 36 are effectively fixed in axial position. Similarly, the higher spring constant distal section may also comprise one or more hypotubes attached over a portion(s) of the distal section, thereby reducing the length of the distal section that may be elongated during rotation as the hypotubes fix the underlying wire turns or coils of the drive shaft in axial position. These hypotube(s) 36 also work to resist and/or minimize the loss of build tensioning force built into the drive shaft in certain embodiments. The same effect may be realized by providing one or more hypotubes 36 at spaced-apart location(s) along the distal section 34. In some cases, and as illustrated in FIG. 3, a hypotube 36 may overlap or straddle both the proximal section 32 and the distal section.

In some embodiments, hypotubes 36 may be employed in. e.g., the drive shaft 26 of FIG. 1 wherein the spring constant of the drive shaft is the same along its length.

There is a spacing between adjacent hypotubes 36, when two or more hypotubes 36 are used as in FIG. 3. The spaced-apart hypotubes 36 allow the drive shaft 26 to have good bending, flexibility characteristics to help traverse tortuous vasculature while providing the benefits described above.

FIG. 4 illustrates an additional structure, one or more mandrels 38, located within the drive shaft lumen at the proximal section 32 and attached by swaging or other known method to the inner surface of the drive shaft 26 defining the lumen, thereby effectively fixing the portions of the drive shaft 26 attached to the mandrels 38 fixed in axial location. These mandrel(s) 38 may be provided in the regions that are not covered by hypotubes 36 to provide additional support and resistance to bending and/or elongation and/or reduction in build tensioning force in the lower spring constant proximal section 32. In addition, the presence of the mandrel(s) 38 resists the drive shaft 26 wrapping over upon itself with looping and/or wrapping of the drive shaft 26. As shown, there may be a spacing between adjacent mandrels 38 that allows proximal section 32 of drive shaft 26 to retain its lower spring constant, as the drive shaft 26 is able to stretch in the region between the spaced-apart mandrels 38, to provide a bending capability that assists in traversing the patient's vasculature. Mandrels 38 may also be used with the same benefits in the distal section 34.

The hypotube(s) may be used with, or without the mandrel(s) to achieve the stated objectives and advantages. Similarly, the mandrel(s) 38 may be used with, or without the hypotube(s) 36 to achieve the stated advantages.

The skilled artisan will appreciate that the hypotube and/or mandrel disclosures provided herein will readily apply to provide the stated benefits to elongated drive shafts used in rotational atherectomy and/or thrombectomy devices.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A hemodynamic support device comprising: an electric motor having a rotational motor shaft and motor manifold at least partially surrounding the rotational motor shaft, the electric motor configured to rotate the rotational motor shaft; a blood pump comprising an impeller, an impeller shaft and impeller housing at least partially surrounding the impeller and part of the impeller shaft; an elongated flexible drive shaft formed of a plurality of wire filars and having an undeformed length, a proximal end and a distal end, the proximal end of the drive shaft rotationally connected to the rotational motor shaft and the distal end rotationally connected to the impeller shaft;
wherein the elongated flexible drive shaft is deformed to a stretched configuration with a length greater than the undeformed length between the rotational motor shaft and impeller shaft to create a biasing build tension force between the impeller and the electric motor shaft, wherein the impeller resists movement in a distal axial direction within the impeller housing as a result of the biasing build tension force.

2. The hemodynamic support device of claim 1, wherein the impeller housing comprises an inner surface and the impeller comprises a proximal surface, and wherein the biasing build tension force maintains the impeller's proximal surface in contact with the inner surface of the impeller housing.

3. The hemodynamic support device of claim 1, wherein an axial location of the impeller is maintained as a result of the biasing build tension force.

4. The hemodynamic support device of claim 1, wherein the biasing build tension force is within the range of 20 grams to 500 grams.

5. The hemodynamic support device of claim 4, wherein the biasing build tension force is within the range of 220 grams to 240 grams.

6. The hemodynamic support device of claim 1, further comprising an outer sheath connected with the impeller housing and the motor manifold.

7. The hemodynamic support device of claim 6, further comprising an inner sheath disposed within the outer sheath and surrounding at least part of the length of the drive shaft.

8. The hemodynamic support device of claim 1, further comprising the drive shaft being configured to remove constructional stretch by stretching the shaft axially with an applied force between 20 grams and 500 grams, then removing the applied force.

9. The hemodynamic support device of claim 1, wherein the flexible drive shaft comprises one or more hypotubes surrounding a portion of a length of the proximal section, wherein each of the one or more hypotubes are attached to the wire filars of the drive shaft and configured to fix the wire filars attached to the one or more hypotubes in an axial position relative to each other.

10. The hemodynamic support device of claim 1, wherein the drive shaft further comprises:
a proximal section having a length and a spring constant, and
a distal section having a length that is longer than the proximal section length and
a spring constant that is greater than the proximal section spring constant.

11. The hemodynamic support device of claim 1, wherein the drive shaft further comprises
one or more hypotubes surrounding a portion of the length of a distal section, wherein each of the one or more hypotubes are attached to the wire filars of the drive shaft and configured to fix the wire filars that are attached to the one or more hypotubes in an axial position relative to each other.

12. The hemodynamic support device of claim 1, wherein the drive shaft defines an inner lumen therethrough, wherein at least one support mandrel is disposed and attached to the wire filars of the drive shaft within the inner lumen, and wherein the wire filars attached to the at least one support mandrel are configured to be fixed in axial position relative to each other.

13. A flexible drive shaft assembly for an intravascular medical device comprising:
   a proximal section having a length and a spring constant, and
   a distal section having a length that is longer than the proximal section length and
   a spring constant that is greater than the proximal section spring constant.

14. The drive shaft assembly of claim 13, further comprising one or more hypotubes surrounding a portion of the length of the proximal section, wherein each of the one or more hypotubes are attached to the wire filars of the drive shaft and configured to fix the wire filars attached to the one or more hypotubes in an axial position relative to each other.

15. The drive shaft assembly of claim 14, further comprising one or more hypotubes surrounding a portion of the length of the distal section, wherein each of the one or more hypotubes are attached to the wire filars of the drive shaft and configured to fix the wire filars that are attached to the one or more hypotubes in an axial position relative to each other.

16. The drive shaft assembly of claim 13, wherein the drive shaft assembly further defines an inner lumen therethrough, and comprising at least one support mandrel attached to the wire filars of the proximal section within the inner lumen, and wherein the wire filars attached to the at least one support mandrel are configured to be fixed in axial position relative to each other.

17. The drive shaft assembly of claim 13, wherein the drive shaft assembly further defines an inner lumen therethrough, and comprising at least one support mandrel attached to the wire filars of the distal section within the inner lumen, and wherein the wire filars attached to the at least one support mandrel are configured to be fixed in axial position relative to each other.

18. The flexible drive shaft assembly of claim 13, wherein the intravascular medical device comprises one or more of the group consisting of: a blood pump, a rotational atherectomy device, and a rotational thrombectomy device.

19. A flexible drive shaft assembly for an intravascular medical device comprising:
   a proximal section having a length and a spring constant;
   a distal section having a length that is longer than the proximal section length and a distal section spring constant that is greater than the proximal section spring constant;
   one or more hypotubes surrounding a portion of the length of the proximal section and/or distal section, wherein each of the one or more hypotubes are attached to a plurality of wire filars of the drive shaft assembly and configured to fix the wire filars attached to the one or more hypotubes in an axial position relative to each other,
   wherein the drive shaft assembly further defines an inner lumen therethrough, and comprising at least one support mandrel attached to the wire filars of at least one of the proximal and distal section within the inner lumen, and wherein the wire filars attached to the at least one support mandrel are configured to be fixed in axial position relative to each other.

20. The flexible drive shaft assembly of claim 19, wherein the intravascular medical device comprises one or more of the group consisting of: a blood pump, a rotational atherectomy device, and a rotational thrombectomy device.

* * * * *